United States Patent
Starke et al.

(10) Patent No.: US 10,517,970 B2
(45) Date of Patent: Dec. 31, 2019

(54) METHOD AND APPARATUS FOR STERILIZING A DIALYZER

(71) Applicant: B. BRAUN AVITUM AG, Melsungen (DE)

(72) Inventors: Christian Starke, Radeberg (DE); Sina Burkert, Dresden (DE)

(73) Assignee: B. Braun Avitum AG (DE)

( * ) Notice: Subject to any disclaimer, the term of this patent is extended or adjusted under 35 U.S.C. 154(b) by 178 days.

(21) Appl. No.: 15/682,036

(22) Filed: Aug. 21, 2017

(65) Prior Publication Data

US 2018/0050121 A1  Feb. 22, 2018

(30) Foreign Application Priority Data

Aug. 22, 2016  (DE) ................. 10 2016 115 498

(51) Int. Cl.
*A61L 2/03* (2006.01)
*A61M 1/16* (2006.01)

(52) U.S. Cl.
CPC ............. *A61L 2/03* (2013.01); *A61M 1/1682* (2014.02); *A61L 2202/11* (2013.01); *A61L 2202/24* (2013.01)

(58) Field of Classification Search
CPC .................................. A61M 1/168; A61L 2/03
See application file for complete search history.

(56) References Cited

U.S. PATENT DOCUMENTS

| 5,462,644 A | 10/1995 | Woodson |
| 2002/0168456 A1 | 11/2002 | Robbins |
| 2004/0022669 A1 | 2/2004 | Ruan et al. |
| 2010/0112151 A1 | 5/2010 | Bluestein et al. |
| 2012/0118338 A1* | 5/2012 | Nakanishi ............. A61B 1/121 134/166 C |
| 2017/0138833 A1 | 5/2017 | Burkett |

FOREIGN PATENT DOCUMENTS

| DE | 202011105738 U1 | 12/2012 |
| DE | 102015120003 A1 | 6/2017 |

OTHER PUBLICATIONS

German Search Report for German Application No. 10 2016 115 498.9, with translation, dated Aug. 16, 2017—14 Pages.
Extended European Search Report for European Application No. 17 187 119.7, dated Jan. 23, 2018, including English translation, 8 pages.

\* cited by examiner

*Primary Examiner* — Donald R Spamer
(74) *Attorney, Agent, or Firm* — RatnerPrestia

(57) ABSTRACT

An apparatus for sterilizing a dialyzer for extracorporeal blood treatment includes a pulsed electric field generator arranged for generating a pulsed electric field penetrating the dialyzer received between a first electrode and a second electrode, when a pulsed electric voltage is applied between the first electrode and the second electrode of the generator. A method of sterilizing a dialyzer for extracorporeal blood treatment adapted to be executed using the apparatus incorporates, in a process for preparing or manufacturing the dialyzer, at least the steps of generating a pulsed electric field using a predetermined number of electric pulses of defined electric voltage, defined pulse duration and defined pulse-off time between the pulses, and applying the pulsed electric field to the dialyzer.

14 Claims, 3 Drawing Sheets

METHOD AND APPARATUS FOR STERILIZING A DIALYZER

CROSS REFERENCE TO RELATED APPLICATIONS

This application claims priority to German application DE 10 2016 115 498.9 filed Aug. 22, 2016, the contents of such application being incorporated by reference herein.

FIELD OF THE INVENTION

The invention relates to a method and an apparatus for sterilizing a dialyzer for extracorporeal blood treatment and especially relates to a method and an apparatus for sterilizing such dialyzer with a pulsed electric field.

BACKGROUND OF THE INVENTION

During manufacture of dialyzers, the correct and sufficient sterilization thereof is important to safely kill microorganisms having detrimental effects for a patient, such as bacteria, viruses, fungi and the like.

In accordance with the European Standard (EN) 556, an object can be considered to be sterile when the theoretical value of no more than one living microorganism is present in $1\times10^6$ sterilized units of the final product. For sufficient sterility of dialyzers for extracorporeal blood treatments, therefore e.g. the presence of viable organisms has to be reduced by 6 levels to a sterilization target of the Sterilization Assurance Level (SAL) $10^{-6}$ or SAL 10-6.

Common methods for sterilizing dialyzers are based, for example, on the utilization or use of gamma radiation, electron radiation, ethylene oxide (EtO/EO) and superheated steam. In said methods, radiation, heat and toxicity have a killing effect on microorganisms.

All of the afore known sterilization methods for dialyzers have specific drawbacks, however.

Gamma sterilization, for example, depends on a radioactive isotope ($^{60}$Co or $^{137}$Cs). Procuring the latter is difficult, transport thereof is complicated and an appropriate waste disposal site is required. Gamma radiation systems in addition require very complex measures for shielding the radioactive radiation. Moreover, the radiation process takes several hours due to the low dose rate intrinsic to its operating principle.

Although sterilization by electron radiation requires no radioactive isotope, it requires complex shielding measures due to the deceleration radiation occurring during the process analogously to gamma sterilization. Moreover, for generating electron beams complicated and thus expensive accelerators are necessary to obtain the required penetration depth which for electron beams is substantially lower than for gamma rays.

The ethylene oxide used for EtO sterilization in turn is a strong protoplasmic toxin, it is carcinogenic, mutagenic, allergenic and chemically irritative and consequently highly toxic, cancer-causing and, in addition, highly explosive in a gas mixture with air having an ignition point of only 40°. Thus, it constitutes a considerable risk. Removing the ethylene oxide from the dialyzer after accomplished sterilization is rather time-consuming.

The generation of superheated steam required for superheated steam sterilization finally is energy-consuming and, due to the high temperatures, is a considerable load for the components of the dialyzer. In order to be able to apply superheated steam sterilization, the dialyzer further has to meet specific requirements in terms of design.

Against this background, there is a demand for alternative options for sterilizing especially dialyzers for extracorporeal blood treatments.

SUMMARY OF THE INVENTION

Consequently, an object underlying the invention is to provide an alternative and innovative sterilization method that overcomes the afore-mentioned drawbacks of the known sterilization methods and enables pulsed electric fields (PEF) to be used for sterilization of dialyzers for extracorporeal blood treatment.

In accordance with the invention, this object is achieved by an apparatus and a method comprising the features of the independent claims. Advantageous developments of the invention are the subject matter of the enclosed dependent claims.

In conformity with a general inventive idea, the invention focuses on safely killing germs already present in the dialyzer. In other words, the core of the invention is not intended to consist in sterilizing a medical product or in preventing germs from penetrating a dialyzer, but in satisfactorily killing microbial contamination already present in a dialyzer while reaching respective required SAL values.

For this purpose, with electroporation by an electric field which can be generated, for example, as a short pulse by the discharge current of a capacitor, the cell membrane of cells is rendered permeable by reason of different effects. The temporary permeabilization causes intracellular parts to be released, induced by hydrostatic pressure differences and osmotic effects. Further, substances from the external medium can be received in the interior of the cell.

Said electroporation can be used for inactivating or killing microorganisms. For an object to be treated (dialyzer) a reaction space in which a pulsed electric field is generated by way of one or more pairs of electrodes is formed for this purpose on said object or in the vicinity thereof. The repeat rate of the pulses is adapted to an applied product current. An effective electric field intensity for microorganisms ranges from 10 to 40 kV/cm.

Pulsed electric fields (PEF) as described in the foregoing destroy especially the cell membranes of bacteria and the DNS/RNS of viruses and thus kills the latter.

In accordance with the general inventive idea, a method and an apparatus for technically materializing the method are provided in which a dialyzer is sterilized by pulsed electric fields (PEF) by initially filling the dialyzer with a liquid and then via electrodes introducing pulses of electric current that cause sterilization of the liquid introduced to the dialyzer and thus of the dialyzer.

PEF sterilization of dialyzers is based on the two basic assumptions or preconditions that, on the one hand, the blood chamber of the dialyzer, i.e. all parts getting in contact with blood during a dialysis treatment, have to be sterile, and, on the other hand, the sterilization of a liquid introduced to the dialyzer causes sterilization of the blood chamber of the dialyzer.

For this purpose, electrodes are arranged on two sides of a dialyzer so that the interior of the dialyzer (cut face, fiber interior of the hollow fibers/fibers) constitutes a sterilization chamber and, in this way, directly the liquid present in the dialyzer and, consequently, also directly the blood chamber of the dialyzer itself are sterilized.

In accordance with the invention, PEF sterilization of dialyzers offers advantages to the effect that only low energy (very high voltages but low current intensities and extremely short periods of time (pulse)) is required, that sterilization is possible within very short time, that an inline process, e.g. adapted to be integrated in a fiber integrity test, is possible, that, advantageously especially with respect to radioactive radiation sources, there is a possibility of switch-off, and/or that any use of hazardous substances such as radioactive isotopes or ethylene oxide may be dropped.

In detail, an object is achieved by an apparatus for sterilizing a dialyzer for extracorporeal blood treatment comprising a unit for generating a pulsed electric field (pulsed electric field generator) which is arranged, when applying pulsed electric voltage between a first electrode and a second electrode of said unit, for generating a pulsed electric field penetrating the dialyzer received between the first electrode and the second electrode. For this purpose, the apparatus may advantageously be configured of several parts and for the sterilizing operation may be adapted to be temporarily coupled to the dialyzer as part of a preparation or manufacturing process of the dialyzer, or may be arranged, in the manner of a fixed installation, as a defined space along a process chain through which the dialyzer can be passed during the preparation or manufacturing process or into which the dialyzer can be temporarily introduced.

Of preference, the unit for generating a pulsed electric field includes a first section that is or can be disposed on a first end face of the dialyzer and a second section that is or can be disposed on a second end face of the dialyzer opposed to the first section, and the first electrode is or can be disposed in the first section and the second electrode is or can be disposed in the second section such that the pulsed electric field penetrates at least one hollow fiber bundle accommodated in the dialyzer in the longitudinal direction thereof. In this advantageous embodiment, the liquid inlet and the liquid outlet as well as the electrode, being surrounded by or potted with electric insulation where necessary, are accommodated in the cap-shaped components which provide the required connections and can be fixed to the dialyzer at least for the duration of the sterilizing operation.

Of preference, the first electrode and the second electrode are produced in hollow cylinder shape, the first section of the unit for generating a pulsed electric field includes an electric insulator in which the first electrode is accommodated, the second section of the unit for generating a pulsed electric field includes an electric insulator in which the second electrode is accommodated, and a liquid channel opening into the dialyzer and toward the outside of the unit for generating a pulsed electric field extends through each of the first section and the second section of the unit for generating a pulsed electric field. In this way, the required liquid can advantageously be supplied and discharged on the end face of the dialyzer.

Of preference, the liquid channel opening into the dialyzer extends in the direction of the longitudinal axis of the dialyzer through the insulator and through the hollow cylinder of the electrode, the liquid channel being insulated against the electrode by the insulator.

Alternatively preferred, the first electrode and the second electrode are produced in disc shape, the first section of the unit for generating a pulsed electric field includes an electric insulator in which the first electrode is accommodated, the second section of the unit for generating a pulsed electric field includes an electric insulator in which the second electrode is accommodated and a liquid channel opening into the dialyzer and toward the outside of the unit for generating a pulsed electric field extends through each of the first section and the second section of the unit for generating a pulsed electric field.

Of preference, in the foregoing alternative the liquid channel opening into the dialyzer extends along a first length in the direction of the longitudinal axis of the dialyzer and along a second length in the direction of the transverse axis of the dialyzer between the dialyzer and the electrode through the insulator. Advantageously, in this way the required liquid can be supplied and discharged on the side of the dialyzer.

It is understood that the afore-mentioned alternatives can be combined, i.e. respective liquid channels may be provided on one side of the dialyzer at the end face and on another side of the dialyzer laterally thereof. This entails advantageous additional degrees of freedom for different dialyzers and/or process environments, for example.

Of preference, the unit for generating a pulsed electric field can be fixed to the dialyzer in a fluid-tight manner with a screw-on thread arrangement.

As a preferred alternative, the unit for generating a pulsed electric field and the dialyzer are adapted to be connected in a fluid-tight manner by a sealing face surrounding the hollow fiber bundle on the inside of the wall of the dialyzer in the area of a cut face of the hollow fiber bundle and by an elevation adapted to be pressed against the sealing face. Coupling of a pulse field generating unit and of the dialyzer on the basis of pressure advantageously facilitates automation of the sterilizing process, as the rotational movement of a screwing operation may be dropped and coupling may be performed by only a linear feeding and removing motion.

As a preferred alternative, the unit for generating a pulsed electric field includes a first section and a second section which are arranged opposed to each other along the longitudinal side of the dialyzer, and the first electrode is disposed in the first section and the second electrode is disposed in the second section so that the pulsed electric field penetrates at least the hollow fiber bundle accommodated in the dialyzer in the transverse direction thereof. The arrangement of the electrodes along the longitudinal side of the dialyzer advantageously enables a sterilizing chamber to be fixedly installed in the process chain and unnecessary manipulation of the dialyzer to be avoided. Moreover, the distance of the electrodes which is smaller as compared to the afore-explained configuration variants results in a reduction of the electric field intensity required for reaching the sterilization level and thus facilitates generation thereof.

In the afore-mentioned alternative, the first electrode and the second electrode are preferably flatly plate-shaped and are arranged in parallel to each other. A plate-shaped flat electrode form may advantageously allow for precisely predetermining the electric field to be generated independently of the shape of the dialyzer.

As a preferred alternative, in the afore-mentioned alternative the first electrode and the second electrode are curved following the circumference of the dialyzer. A bent electrode shape may advantageously allow for precisely adapting the electric field to be generated to the actual dialyzer shape.

An object is also achieved by a method of sterilizing a dialyzer for extracorporeal blood treatment comprising the following steps in a process for preparing or manufacturing the dialyzer: generating a pulsed electric field with a predetermined number of electric pulses of defined electric voltage, defined pulse duration and defined pulse-off time between the pulses, and applying the pulsed electric field to the dialyzer.

Preferably, the method further comprises the steps of: arranging, prior to generating the pulsed electric field, a unit for generating a pulsed electric field on both sides of the dialyzer; and filling the dialyzer with a predetermined liquid prior to generating the pulsed electric field; and, after removing said pulsed electric field, allowing a predetermined exposure time for reactive substances generated by the electric pulses to elapse; and flushing the dialyzer for removing residues of the sterilizing process.

Preferably, the foregoing method is carried out by an apparatus of any one of the afore-mentioned embodiments.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
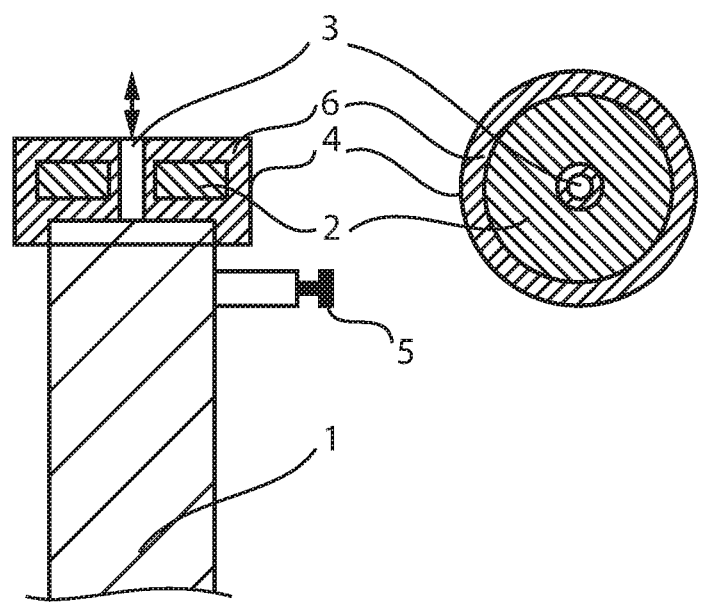
FIG. 1 schematically shows a sectional view of a dialyzer including a PEF unit, a top-side liquid inlet and, respectively, liquid outlet and electrodes on an end face of the dialyzer according to a first embodiment of the invention.

It is noted that in the drawings like or equally acting elements and components are denoted with like reference numerals and are not redundantly described.

FIG. 1 schematically shows a sectional view of a dialyzer 1 including a PEF unit 4, a top-side liquid inlet and, respectively, liquid outlet 3 and at least two electrodes 2 on an end face of the dialyzer according to a first embodiment. A laterally arranged plug located in the dialysis solution nozzle is denoted with reference numeral 5.

The PEF unit 4 is a unit for generating a pulsed electric field which is arranged to generate a pulsed electric field penetrating the (liquid-filled) dialyzer 1 in a predetermined manner by applying electric pulses of predetermined form, duration and/or signal intensity (voltage) with the electrodes 2.

The dialyzer 1 is filled with a liquid, preferably purified or distilled water of predetermined purity. The predetermined purity is useful, as in the case of an impure solution or liquid an undesired dielectric breakdown may occur when the pulsed electric field is applied. Various additives may be added to the liquid, such as chorine-containing substances for increasing the sterilizing effect and thus reduction of the sterilizing time. In this context, the related increase in the conductivity of the liquid has to be considered and has to be taken into account when defining the required electric field intensity. In the case of excessive electric conductivity of the liquid, a dielectric breakdown may occur which in turn may entail impairment or damage of the dialyzer and/or of the PEF unit.

An electrode 2 is arranged on each side of the dialyzer 1 via the end or cut face thereof and is accommodated in the PEF (pulsed electric field) unit 4.

In other words, the dialyzer 1 includes on its respective other end face not shown in FIG. 1 an at least functionally mirror-inverted arrangement having a first top-side electrode 2 and a corresponding second bottom-side electrode (not shown). Hereinafter, therefore the electrodes 2 of the pair of electrodes on the dialyzer 1 are described in the singular form and it is understood that the description nevertheless relates to both electrodes 2 of the pair of electrodes on the dialyzer 1.

In this embodiment, the electrode 2 has an annular or (hollow) cylindrical shape the diameter of which preferably corresponds at least to the diameter of the hollow fiber bundle (potted with polyurethane (PUR), for example) inside the dialyzer 1 so that, when an electric voltage is applied to the electrode 2, a homogenous electric field forms inside the dialyzer 1 between the first top-side electrode 2 and the second bottom-side electrode (not shown).

The electrode 2 is provided with a respective insulation 6 that fills, for example, a remaining recess of the PEF unit 4. In addition, the electrode 2 includes a hole, preferably in the form of a central bore, through which liquid can be introduced and discharged during a filling and/or flushing process. The electrode 2 and the insulation 6 in this embodiment form a unit together with e.g. an outer sheath of the PEF unit 4. The PEF unit 4 may as well be a PEF adapter.

The PEF unit 4 or the PEF adapter, respectively, allows for sealing the liquid-filled chamber toward the housing of the dialyzer 1. For this purpose, the PEF unit 4 preferably includes a female thread which as to its design and dimensioning corresponds to the thread of a blood cap for the dialyzer 1.

At the beginning of a sterilizing treatment, a PEF unit 4 is screwed onto each of the two (end) faces of the dialyzer 1 (without blood caps). As an additional sealing measure, an O-ring may be provided analogously to the sealing of blood caps. The production process of the dialyzer 1 may expediently take place such that the assembly of blood cap follows sterilization.

In the further sterilizing treatment, the dialyzer 1 is filled with liquid and upon reaching a predetermined filling level it is uncoupled from the liquid supply.

After that, the PEF treatment is carried out. In the PEF treatment, a defined number of electric pulses of defined field intensity (or voltage), defined pulse duration and defined pulse-off time between the pulses is applied to the dialyzer 1, or the liquid provided in the dialyzer, respectively, via the electrodes 2 along the longitudinal direction of the dialyzer.

The electric pulses are generated by a technology for generating high-frequency pulses of high electric voltage known per se (e.g. with a Marx generator). The technology known per se therefore will not be redundantly described here.

After PEF treatment as described before, preferably a dwell time is provided during which reactive substance generated by the voltage pulses (reactive oxygen species, elementary chlorine (when chloric compounds are added to the liquid) etc.) can be active so as to increase the effect of sterilization. Subsequently, the dialyzer 1 is flushed with distilled or purified water so as to remove residues such as e.g. killed microorganisms, added substances and the like.

In conformity with the first embodiment, PEF sterilization may be incorporated in the production process of a dialyzer 1 as described below.

After initiating steps, the dialyzer can be cut including a check of the cut faces. After that, the dialyzer 1 (without blood caps) can be connected to a device for checking fiber integrity (not shown) and appropriate test steps can be carried out. Then the connection of the dialyzer (without blood caps) to an apparatus for PEF sterilization may be provided and the sterilization may be carried out. Furthermore, the dialyzer 1 (without blood caps) then can be connected to a device for drying the dialyzer 1 and the dialyzer 1 can be dried.

Finally, sterilized blood and protective caps are attached to the dialyzer 1. For ensuring the sterility of the blood chamber the insides of blood caps and protective caps as well as the O-ring preferably have to be superficially sterilized. Further steps of a regular production process for completing the dialyzer 1 may follow.

Preferably, the process steps of the fiber integrity test, of PEF sterilization and of drying can be carried out in a combined manner.

Moreover, the liquid present in the dialyzer 1 can be circulated during the PEF treatment so as to distribute sterilizing substances formed, such as reactive oxygen species, elementary chlorine and the like, evenly over all areas and/or hollow fibers of the dialyzer 1.

In a modification, the PEF treatment can further be carried out in intervals, and accordingly, periods and times or intervals of the PEF treatment and periods and times or intervals in which the liquid is circulated may alternate.

Figure 2:
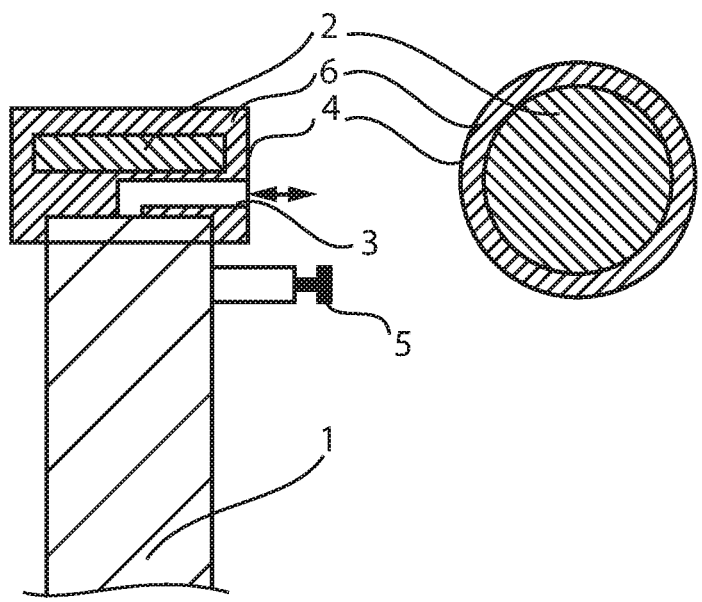
FIG. 2 schematically shows a sectional view of a dialyzer including a PEF unit and a lateral liquid inlet and, respectively, liquid outlet according to a second embodiment of the invention.

FIG. 2 schematically shows a sectional view of a dialyzer 1 comprising a PEF unit 4, an insulation 6 and a lateral liquid inlet and, respectively, liquid outlet 3 according to a second embodiment of the invention. The plug 5 in the dialysis solution nozzle, too, is provided on a sidewall of the dialyzer 1.

The second embodiment of the dialyzer 1 comprising the PEF unit 4 differs from that of the first embodiment in that the liquid can be introduced to and discharged from the dialyzer through a channel opening laterally below the electrode 2 in an opening or, respectively, in the liquid inlet or liquid outlet 3 in the insulation 6 and therefore the electrode 2 is disk-shaped, i.e. it has no central bore.

The preceding description of the first embodiment is fully applicable to the second embodiment as well.

Figure 3:
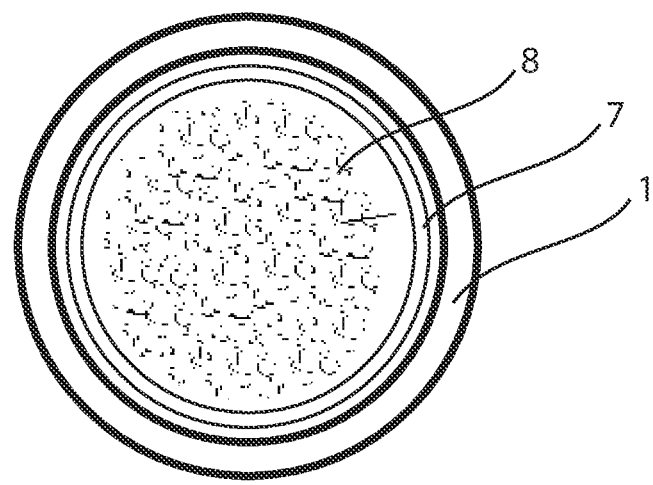
FIG. 3 schematically shows a modification of the first and second embodiments including an alternative sealing of a liquid-filled chamber of the dialyzer according to a third embodiment.

FIG. 3 schematically illustrates a modification of the first and second embodiments with alternative sealing of the liquid-filled chamber of the dialyzer 1 according to a third embodiment.

In the third embodiment, the arrangement of the PEF unit 4 on the dialyzer 1 and the sealing of the liquid-filled chamber on the transition between the PEF unit 4 and the dialyzer 1 are not carried out, other than in the first and second embodiments, with a thread but by pressing a hollow cylinder (not shown) of thin wall thickness onto the area between the housing and the fiber-containing cut face 8 of the dialyzer 1.

For this purpose, the area between the housing and the fiber-containing cut face of the dialyzer 1 may be in the form of a sealing face 7, and the hollow cylinder may be provided in the PEF unit 4 for this purpose.

The preceding description of the first and second embodiments is fully applicable to the third embodiment, too.

Figure 4:
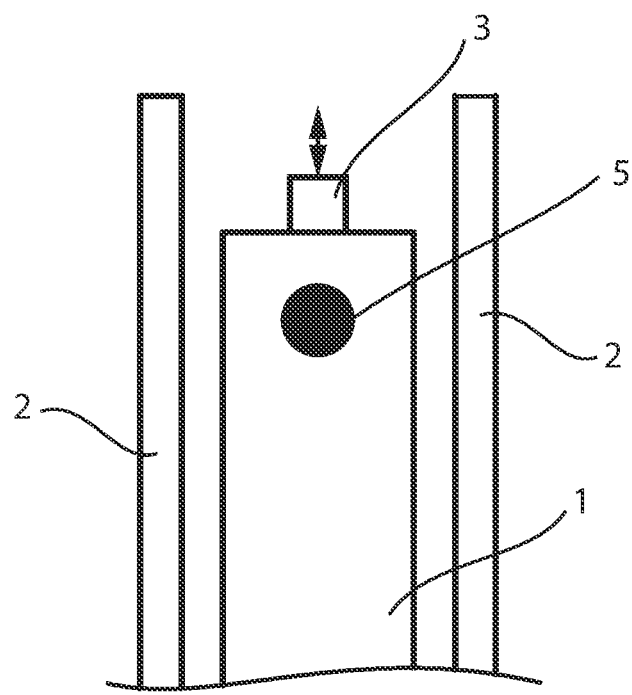
FIG. 4 schematically shows a sectional view of a dialyzer including a PEF unit, a top-side liquid inlet and, respectively, liquid outlet and electrodes along the longitudinal sides of the dialyzer according to a fourth embodiment of the invention.

FIG. 4 schematically illustrates a sectional view of a dialyzer 1 comprising a PEF unit 4, a top-side liquid inlet and, respectively, liquid outlet and electrodes 2 at a predetermined distance on the outside along the longitudinal sides of the dialyzer 1 in accordance with a fourth embodiment of the invention.

In the fourth embodiment, the electrodes 2 are not arranged, in contrast to the first to third embodiments, on the respective end faces of the dialyzer 1 but in the form of parallel plates on or along the longitudinal sides thereof. The electrodes 2 therefore generate pulsation along the transverse direction of the dialyzer 1 in this embodiment.

In simulations of the electric field forming in this case it can be demonstrated that with electrodes 2 in the form of flat plates an approximately homogenous electric field forms therebetween and the electric field intensity decreases in the respective marginal areas only. Said decrease may be compensated, however, by dimensioning the electrodes 2 to be slightly larger than the cross-sectional area of the dialyzer 1, as illustrated in FIG. 4.

Figure 5:
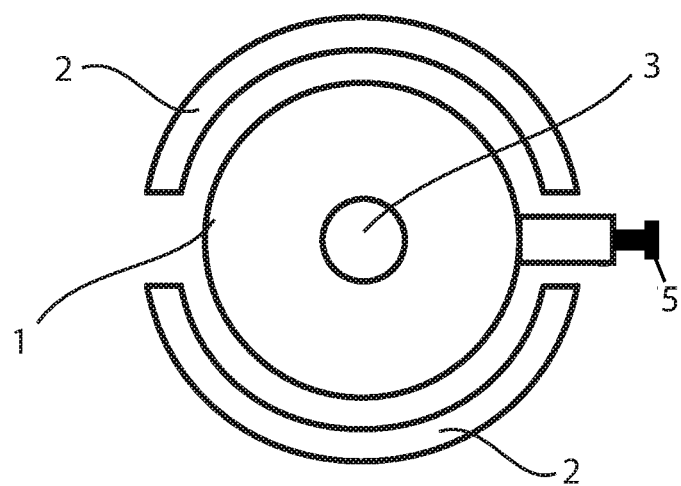
FIG. 5 schematically shows a top view onto a dialyzer including a PEF unit and a curved electrode contour according to a fifth embodiment.

FIG. 5 schematically illustrates a top view onto a dialyzer 1 comprising a PEF unit 4 and curved electrodes 2 according to a fifth embodiment. The fifth embodiment constitutes a modification of the fourth embodiment in which the electrodes 2 arranged on the outside are curved corresponding to the periphery and/or the radius of the dialyzer 1 and are arranged at a predetermined distance from the circumferential wall of the dialyzer 1.

When designing the electrodes 2 in the form of curved plates, in the space between the electrodes 2 in which the dialyzer 1 is located areas of high field intensity and areas of lower field intensity may occur. Therefore, it is possible that the effect of sterilization is not evenly distributed throughout the entire dialysis volume. Such uneven distribution of the effect of sterilization may be counteracted in a minimizing and/or compensating manner by reducing the inhomogeneity of the electric field with a further adapted and/or specific formation of the electrodes 2 and/or time variation of locally forming field maximums and field minimums to generate field-induced turbulence.

The foregoing description of the first and second embodiments is fully applicable to the fourth and fifth embodiments, too.

The PEF unit 4 according to the first to third embodiments and, respectively, the electrodes 2 according to the fourth and fifth embodiments currently are not provided to be permanently maintained on a dialyzer intended for practical use, but are used during a manufacturing process of the dialyzer 1 merely temporarily for sterilization thereof and especially for removal of germs already present in the dialyzer 1.

Therefore, in the third embodiment it is sufficient to press the PEF unit 4 (adapter) against a support area sealing in a predetermined manner on the dialyzer 1. It is thus understood that in the afore-described embodiments fastening devices, pressing devices, holding fixtures and the like may be expertly provided additionally or alternatively to described embodiments so as to maintain components involved in performed process steps and embodiments in situ and fluid-tight in a predetermined manner, without any detailed description of such devices and means being required.

Moreover, in the fourth and fifth embodiments, the plate-shaped electrodes 2 and, respectively, the curved or bent electrodes 2 may be arranged and dimensioned so that during the PEF process steps the dialyzer 1 can be guided between the electrodes 2 in an automated manner and, after a predetermined dwell time, can be guided out of the electrode space. Therefore, predetermined clearances between the electrodes 2 or a predetermined positioning of the dialyzer 1 between the electrodes 2 may be provided, as it is indicated, for example, in FIG. 4 and FIG. 5 by the position of the dialysis fluid nozzle relative to the electrodes 2.

It is noted that, due to the lack of physical contact of the PEF unit 4 and the liquid, the electric insulation 6 in the fourth and fifth embodiments may be omitted, where appropriate.

As described in the foregoing, an apparatus for sterilizing a dialyzer for extracorporeal blood treatment comprises a unit for generating a pulsed electric field which is arranged for generating a pulsed electric field penetrating the dialyzer received between the first electrode and the second electrode of the unit, when a pulsed electric voltage is applied between a first electrode and a second electrode.

Accordingly, the unit for generating a pulsed electric field (PEF unit 4) may include a first section disposed on a first end face of the dialyzer and a second section disposed opposite to the first section on a second end face of the dialyzer, and the first electrode may be arranged in the first section and the second electrode may be arranged in the second section so that the pulsed electric field penetrates at least one hollow fiber bundle accommodated in the dialyzer in the longitudinal direction thereof.

In accordance with the first embodiment as afore-described, the first electrode and the second electrode may be produced in hollow cylindrical shape, the first section of the unit for generating a pulsed electric field may include an electric insulator in which the first electrode is accommodated, the second section of the unit for generating a pulsed electric field may include an electric insulator in which the second electrode is accommodated, and a liquid channel opening into the dialyzer and toward the outside of the unit for generating a pulsed electric field may extend through each of the first section and the second section of the unit for generating a pulsed electric field.

In accordance with the first embodiment, furthermore the liquid channel opening into the dialyzer may extend in the direction of the longitudinal axis of the dialyzer through the insulator and through the hollow cylinder of the electrode. The liquid channel in this case may be insulated against the electrode by the insulator.

In accordance with the second embodiment as afore-described, the first electrode and the second electrode may be produced in disk shape, the first section of the unit for generating a pulsed electric field may include an electric insulator in which the first electrode is accommodated, the second section of the unit for generating a pulsed electric field may include an electric insulator in which the second electrode is accommodated, and a liquid channel opening into the dialyzer and toward the outside of the unit for generating a pulsed electric field may extend through each of the first and second sections of the unit for generating a pulsed electric field.

In accordance with the second embodiment, in the foregoing alternative the liquid channel opening into the dialyzer may further extend through the insulator between the dialyzer and the electrode along a first length in the direction of the longitudinal axis of the dialyzer and along a second length in the direction of the transverse axis of the dialyzer.

In accordance with the first and second embodiments, the unit for generating a pulsed electric field can be fixed in a fluid-tight manner to the dialyzer with a screw-on thread arrangement.

In accordance with the third embodiment as afore-described, alternatively the unit for generating a pulsed electric field and the dialyzer may be adapted to be connected or coupled in a fluid-tight manner via a sealing face surrounding the hollow fiber bundle on the inside of the wall of the dialyzer in the area of a cut face of the hollow fiber bundle and via an elevation adapted to be pressed against the sealing face.

In accordance with the fourth embodiment as afore-described, the unit for generating a pulsed electric field may include a first section and a second section which are arranged so as to face each other along the longitudinal side of the dialyzer, and the first electrode may be arranged in the first section and the second electrode may be arranged in the second section so that the pulsed electric field penetrates the hollow fiber bundle accommodated in the dialyzer in the transverse direction thereof. Preferably, in the fourth embodiment the first electrode and the second electrode are flatly plate-shaped and are arranged in parallel to each other.

In accordance with the fifth embodiment as afore-described, the first electrode and the second electrode may be curved following the circumference of the dialyzer.

In a method for sterilizing a dialyzer for extracorporeal blood treatment, during a process for preparing or manufacturing the dialyzer the following steps are carried out: generating a pulsed electric field with a predetermined number of electric pulses of defined electric voltage, defined pulse duration and defined pulse-off time between the pulses, and applying the pulsed electric field to the dialyzer.

Prior to generating the pulsed electric field, a unit for generating a pulsed electric field may be arranged on both sides of the dialyzer and the dialyzer may be filled with a predetermined liquid prior to generating the pulsed electric field. After switching off or removing said pulsed electric field it may be provided to allow a predetermined exposure time for reactive substances generated by the electric pulses to expire, and then flushing of the dialyzer may be carried out to remove residues of the sterilization process. Preferably, the afore-mentioned method is carried out by an apparatus of any one of the afore-described embodiments.

As described before, an apparatus for sterilizing a dialyzer for extracorporeal blood treatment comprises a unit for generating a pulsed electric field which is arranged for generating a pulsed electric field penetrating the dialyzer received between the first electrode and the second electrode, when a pulsed electric voltage is applied between a first electrode and a second electrode of the unit. A method for sterilizing a dialyzer for extracorporeal blood treatment adapted to be executed using said apparatus incorporates, in a process for preparing or manufacturing the dialyzer, at least the steps of generating a pulsed electric field with a predetermined number of electric pulses of defined electric voltage, defined pulse duration and defined pulse-off time between the pulses, and applying the pulsed electric field to the dialyzer.

The invention has been described in the foregoing by way of preferred embodiments. It is understood that details of the described preferred embodiments do not restrict the invention per se and various changes, modifications and/or equivalents obvious to those skilled in the art may result all of which as such are within the scope of the invention defined by the attached claims.

The invention claimed is:

1. An apparatus for sterilizing a dialyzer for extracorporeal blood treatment, the apparatus comprising:

a dialyzer having a liquid channel therein;
a first electrode and a second electrode adapted to receive the dialyzer there between, wherein the liquid channel is electrically insulated from the first electrode and the second electrode; and
a pulsed electric field generator coupled to the first and the second electrode, the pulsed electric field generator configured to generate a pulsed electric field that penetrates the dialyzer received between the first electrode and the second electrode by applying a pulsed electric voltage between the first electrode and the second electrode.

2. The apparatus according to claim 1, wherein the pulsed electric field generator includes a first section adapted to be disposed on a first end face of the dialyzer and a second section adapted to be disposed opposite to the first section on a second end face of the dialyzer.

3. The apparatus according to claim 2, wherein the first electrode is arranged in the first section and the second electrode is arranged in the second section so that the pulsed electric field penetrates at least one hollow fiber bundle accommodated in the dialyzer in the longitudinal direction thereof.

4. The apparatus according to claim 2, wherein:
the liquid channel opens into the dialyzer and towards an outside of the pulsed electric field generator, and extends through each of the first section and the second section of the pulsed electric field generator;
wherein the first electrode and the second electrode have a hollow cylindrical shape, the first section of the pulsed electric field generator includes a first electric insulator in which the first electrode is received, and the second section of the pulsed electric field generator includes a second electric insulator in which the second electrode is received.

5. The apparatus according to claim 4, wherein the liquid channel opening into the dialyzer extends in a direction of a longitudinal axis of the dialyzer through the electric insulator and through the hollow cylindrical shape of at least one of the first electrode or the second electrode.

6. The apparatus according to claim 2, further comprising:
a liquid channel opening into the dialyzer and toward the outside of the pulsed electric field generator that extends through each of the first section and the second section of the pulsed electric field generator;
wherein the first electrode and the second electrode are disk shapes, the first section of the pulsed electric field generator includes a first electric insulator in which the first electrode is received, and the second section of the pulsed electric field generator includes a second electric insulator in which the second electrode is received.

7. The apparatus according to claim 6, wherein the liquid channel opening into the dialyzer extends along a first length in the direction of a longitudinal axis of the dialyzer and along a second length in the direction of a transverse axis of the dialyzer between the dialyzer and the first electrode through the first electric insulator.

8. The apparatus according to claim 1, wherein the pulsed electric field generator can be fixed to the dialyzer in a fluid-tight manner by a screw-on thread arrangement.

9. The apparatus according to claim 1, wherein the pulsed electric field generator and the dialyzer are connectable in a fluid-tight manner via a sealing face surrounding a hollow fiber bundle of the dialyzer in an area of a cut face of the hollow fiber bundle on an inside of a wall of the dialyzer and via an elevation adapted to be pressed against the sealing face.

10. The apparatus according to claim 1, wherein the pulsed electric field generator includes a first section and a second section which are arranged opposite to each other along a longitudinal side of the dialyzer, and the first electrode is arranged in the first section and the second electrode is arranged in the second section so that the pulsed electric field penetrates at least a hollow fiber bundle accommodated in the dialyzer in the transverse direction thereof.

11. The apparatus according to claim 10, wherein the first electrode and the second electrode are each plate-shaped and are arranged parallel to each other.

12. The apparatus according to claim 10, wherein the first electrode and the second electrode are curved following a circumference of the dialyzer.

13. An apparatus for sterilizing a dialyzer for extracorporeal blood treatment, the apparatus comprising:
a dialyzer;
a first electrode and a second electrode adapted to receive the dialyzer there between; and
a pulsed electric field generator coupled to the first electrode and the second electrode, the pulsed electric field generator configured to generate a pulsed electric field that penetrates the dialyzer received between the first electrode and the second electrode by applying a pulsed electric voltage between the first electrode and the second electrode;
wherein:
the pulsed electric field generator includes a first section adapted to be disposed on a first end face of the dialyzer and a second section adapted to be disposed opposite to the first section on a second end face of the dialyzer,
a liquid channel opening into the dialyzer and towards an outside of the pulsed electric field generator extends through each of the first section and the second section of the pulsed electric field generator, and
the first electrode and the second electrode have a hollow cylindrical shape, the first section of the pulsed electric field generator includes a first electric insulator in which the first electrode is received, and the second section of the pulsed electric field generator includes a second electric insulator in which the second electrode is received.

14. An apparatus for sterilizing a dialyzer for extracorporeal blood treatment, the apparatus comprising:
a dialyzer;
a first electrode and a second electrode adapted to receive the dialyzer there between; and
a pulsed electric field generator coupled to the first electrode and the second electrode, the pulsed electric field generator configured to generate a pulsed electric field that penetrates the dialyzer received between the first electrode and the second electrode by applying a pulsed electric voltage between the first electrode and the second electrode;
wherein:
the pulsed electric field generator includes a first section adapted to be disposed on a first end face of the dialyzer and a second section adapted to be disposed opposite to the first section on a second end face of the dialyzer,
a liquid channel opening into the dialyzer and toward the outside of the pulsed electric field generator that extends through each of the first section and the second section of the pulsed electric field generator, and the first electrode and the second electrode are disk shapes, the first section of the pulsed electric field generator includes a first electric insulator in which the first electrode is received, and the second section of the pulsed electric field generator includes a second electric insulator in which the second electrode is received.

* * * * *